United States Patent
Wietelmann et al.

(10) Patent No.: US 9,227,987 B2
(45) Date of Patent: Jan. 5, 2016

(54) METHOD FOR PRODUCING AMIDO-ZINC HALIDE/ALKALI-METAL HALIDE COMPOUNDS

(75) Inventors: Ulrich Wietelmann, Friedrichsdorf (DE); Peter Rittmeyer, Sulzbach/Taunus (DE); Uwe Lischka, Frankfurt am Main (DE); Alexander Murso, Liebenburg (DE); Florian Kiefer, Goslar (DE)

(73) Assignee: Rockwood Lithium GmbH (DE)

( * ) Notice: Subject to any disclaimer, the term of this patent is extended or adjusted under 35 U.S.C. 154(b) by 19 days.

(21) Appl. No.: 14/241,690

(22) PCT Filed: Aug. 30, 2012

(86) PCT No.: PCT/EP2012/066863
§ 371 (c)(1),
(2), (4) Date: Feb. 27, 2014

(87) PCT Pub. No.: WO2013/030278
PCT Pub. Date: Mar. 7, 2013

(65) Prior Publication Data
US 2014/0194626 A1    Jul. 10, 2014

(30) Foreign Application Priority Data
Sep. 2, 2011    (DE) .......................... 10 2011 082 055

(51) Int. Cl.
*C07F 1/02* (2006.01)
*C07F 3/06* (2006.01)

(52) U.S. Cl.
CPC .... *C07F 3/06* (2013.01); *C07F 1/02* (2013.01)

(58) Field of Classification Search
USPC ....................................................... 546/11, 9
See application file for complete search history.

(56) References Cited

U.S. PATENT DOCUMENTS

2011/0288296 A1    11/2011    Knochel et al.

FOREIGN PATENT DOCUMENTS

WO    2010/092096 A1    8/2010

OTHER PUBLICATIONS

Mosrin, M. et al.: TMPZnCl.LiCl: A new active selective base for the direct zincation of sensitive aromatics and heteroaromatics. Org. Letters, vol. 11, pp. 1837-1840, 2009.*

Miller, et al. "A Convenient Oxazole C-2 Protecting Group: The Synthesis of 4- and 5-Substituted Oxazoles via Metalation of 2-Triisopropylsilyloxazoles", J. Org. Chem. 70 (2005), pp. 9074-9076.

Valera, et al. "Teh Flow's the Thing . . . Or Is It? Assessing the Merits of Homogeneous Reactions in Flask and Flow", Angew. Chem. Int. Ed., 49 (2010) pp. 2478-2485.

* cited by examiner

*Primary Examiner* — Charanjit Aulakh

(57) ABSTRACT

The invention relates to a method for producing amido-zinc halides as adducts with alkali-metal halides ($R^1R^2N$—$ZnY*LiY$) in aprotic organic solvents, in which a) a primary or secondary amine dissolved in an aprotic organic solvent is provided, b) a lithium base ($R^xLi$) is added in a metered manner, and c) a $ZnY_2$ is subsequently added.

10 Claims, No Drawings

METHOD FOR PRODUCING AMIDO-ZINC HALIDE/ALKALI-METAL HALIDE COMPOUNDS

This application is a §371 of International Application No. PCT/EP2012/066863 filed Aug. 30, 2012, and claims priority from German Patent Application No. 10 2011 082 055.8 filed Sep. 2, 2011.

The present invention relates to a method for preparing amido-zinc halides as an addition product with alkali metal halides ($R^1R^2N$—ZnY*LiY) in aprotic organic solvents.

Aryl- and heteroaryl-metal compounds are prepared either by a halogen-metal exchange reaction (bromine-lithium exchange, for example), insertion of elemental metal into a carbon-halogen bond, for example insertion of zinc into a carbon-iodine bond, or by metalation (deprotonation using strong bases).

However, the cost and limited durability of the aryl- or heteroaryl-iodine compounds are disadvantageous. In addition, in the exchange reactions and insertions, metal salts form which must sometimes be disposed of separately.

The regioselective functionalization of various arenes and heteroarenes is made possible by deprotonation of arenes, and represents one of the most useful conversions in organic synthesis. Organolithium compounds are frequently used for this purpose. However, operations must generally be carried out at very low temperatures to suppress secondary reactions. In addition, some organolithium compounds, such as LiTMP (TMP=2,2,6,6-tetramethylpiperidine) have low stability and therefore are prepared in situ.

Although organomagnesium compounds such as TMPMgCl*LiCl have higher stability, their tolerance toward sensitive functional groups such as aldehydes and nitro groups is limited.

Furthermore, lithium-di-tert-butyl-(2,2,6,6-tetramethylpiperidino)zincate (Li-t-Bu$_2$TMPZn) is known from the literature as a reagent for metalation of aromatics; its high activity is based on a zincate species (Miller, R. A.; Smith, M. R.; Marcune, B.; *J. Org. Chem.* 2005, 70, 9074). Here as well, however, aldehyde functions cannot be tolerated.

The document DE 102010007833 A1 describes the preparation of amido-zinc halides as addition products with alkali metal halides such as TMP-ZnCl*LiCl solution in tetrahydrofuran (THF):

Reacting TMPH (2,2,6,6-tetramethylpiperidine) with n-butyllithium (2.4 M in hexane) in hexane at −40° C.
Reacting the resulting reaction solution at −10° C. with a 1 M solution of ZnCl$_2$ in THF, and heating to 25° C.
Distilling off the THF/hexane solvent mixture under vacuum
Dissolving the resulting solid in pure THF

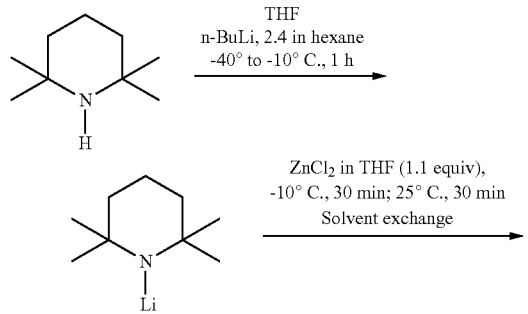

The known method has the following disadvantages:
The need to work at low temperatures, and
A solvent exchange as an additional method step.
During the solvent exchange, a THF/hexane mixture is obtained which must either be laboriously separated by distillation, or disposed of.

The object of the present invention is to provide a method for preparing amido-zinc halide/alkali metal halide which overcomes the disadvantages of the prior art, and to provide a simple and cost-effective method for preparing this class of compounds.

The object is achieved according to the invention by a method for preparing $$R^1R^2N\text{—}ZnY*LiY \quad (I)$$

wherein
$R^1$, $R^2$ are independently selected from H, substituted or unsubstituted aryl or heteroaryl containing one or more heteroatoms, a linear, branched, or cyclic substituted or unsubstituted alkyl, alkenyl, alkynyl, or the silyl derivatives thereof; wherein $R^1$ and $R^2$ may together be part of a cyclic or polymeric structure in which at least one of the radicals $R^1$ and $R^2$ is not H;
Y is selected from the group containing F; Cl; Br; I; CN; SCN; NCO; HalO$_z$, where z is 3 or 4 and Hal is selected from Cl, Br, and I; NO$_3$; BF$_4$; PF$_6$; H; a carboxylate of the general formula $R^xCO_2$; an alcoholate of the general formula $OR^x$; a thiolate of the general formula $SR^x$; $R^xP(O)O_2$; or $SCOR^x$; or $SCSR^x$; $O_mSR^x$, where m is 2 or 3; or $NO_R$, where n is 2 or 3; and derivatives thereof; where $R^x$ is a substituted or unsubstituted aryl or heteroaryl containing one or more heteroatoms, a linear, branched, or cyclic substituted or unsubstituted alkyl, alkenyl, alkynyl, or the derivatives thereof, or H,
in which
a) a primary or secondary amine dissolved in an aprotic organic solvent is provided,
b) a lithium base ($R^xLi$) is metered in, and
c) a ZnY$_2$ is subsequently added.

The ZnY$_2$ is preferably added in solid form.
In one preferred embodiment of the method, the following procedure is carried out:
a) the amine is provided in dissolved form in a concentration range of 10 to 90% by weight and
b) a ZnY$_2$ solution in an aprotic organic solvent and $R^xLi$ are simultaneously metered in,
wherein the dosing of the $R^xLi$ is started first, and only after 5-10 mol-% $R^xLi$ has been added is the metering of the ZnY$_2$ solution begun, and
during the dosing phase, $R^xLi$ and the ZnY$_2$ solution are dosed at different locations in the reaction solution.

The lithium base and the ZnY$_2$ solution should not come into direct contact with one another.

Both methods deliver the amido-zinc halide/alkali metal halide in good yields, even at reaction temperatures>0° C.

The "quasi-simultaneous dosing" in the preferred embodiment variant ensures that TMP-Li which is initially formed is quickly transmetalated and does not have time to attack the solvent THF. The time-delayed dosing ensures that metered-in n-BuLi reacts with the amine.

The method according to the invention is preferably carried out continuously in a micro- or meso-flow reactor.

The R$^x$Li is preferably used as a concentrate (>90% by weight) in an aprotic organic solvent. Due to the use of n-BuLi concentrate, only small quantities of a second solvent are introduced into the product solution.

In addition, the radicals Y are independent of one another, or both are Cl, Br, or I and preferably Cl. n-Butyl-Li is particularly preferably the lithium base. Furthermore, the solvent is preferably selected from cyclic, linear, or branched mono- or polyethers, thioethers, amines, phosphines, and the derivatives thereof which contain one or more further heteroatoms selected from O, N, S, and P, preferably tetrahydrofuran (THF), 2-methyltetrahydrofuran, dibutyl ether, diethyl ether, Pert-butylm ethyl ether, dimethoxyethane, dioxanes, preferably 1,4-dioxane, triethylamine, ethyldiisopropylamine, dimethyl sulfide, dibutyl sulfide; cyclic amides, preferably N-methyl-2-pyrrolidone (NMP), N-ethyl-2-pyrrolidone (NEP), N-butyl-2-pyrrolidone (NBP); cyclic, linear, or branched alkanes and/or alkenes, wherein one or more hydrogen atoms are replaced by a halogen atom, preferably dichloromethane, 1,2-dichloroethane, CCl$_4$; urea derivatives, preferably N,N'-dimethylpropylene urea (DMPU); aromatic, heteroaromatic, or aliphatic hydrocarbons, preferably benzene, toluene, xylene, pyridine, pentane, cyclohexane, hexane, heptane; hexamethylphosphoric triamide (HMPA), CS$_2$, or combinations thereof.

The compounds prepared according to this method are used in synthesis chemistry as selective bases in the deprotonation of functionalized aromatics and heteroaromatics. Compared to lithium amides and magnesium amides, much higher selectivities and yields are achieved when amido-zinc halide/alkali metal halide bases are used. Deprotonation of systems which contain extremely sensitive functional groups such as aldehyde or nitro groups may be carried out. Likewise, sensitive heteroaromatics such as diazines may be selectively deprotonated in high yields. The use of these bases also allows syntheses under noncryogenic conditions.

The subject matter of the invention is explained in greater detail with reference to the following examples.

EXAMPLE 1

95.4 g THF and 14.61 g (103 mmol) 2,2,6,6,-tetramethylpiperidine were placed in a 500-mL double-jacketed reactor. The temperature was set at 20° C. 6.82 g n-butyllithium concentrate (95.5%, 99 mmol) was metered in via a dosing pump over a period of 30 minutes. The jacket temperature of the reactor was regulated so that the internal temperature remained constant at 20° C. Stirring was then continued for an additional 10 minutes at 20° C. 14.14 g (104 mmol) solid zinc chloride was then added in two portions. Due to the strongly exothermic reaction, the reaction temperature quickly rose to 30° C. After the second addition of ZnCl$_2$, stirring was continued for an additional 20 minutes at 20° C.

The cloudy product solution was filtered through a filter until clear.
Starting weight: 128.6 g
Active base: 0.62 mmol/g TMP-ZnCl*LiCl
Yield: 80.5% (relative to n-butyllithium used)

EXAMPLE 2

The test from Example 1 was repeated, but at a reaction temperature of 0° C.
Yield: 87.2%

EXAMPLE 3

140 g (99.1 mmol) 2,2,6,6,-tetramethylpiperidine dissolved in 400 g THF was placed in a 2-L double-jacketed reactor. The temperature was set at 0° C. A total of 64.03 g n-butyllithium concentrate (94.4%, 941 mmol) was metered in via a dosing pump over a period of 70 minutes. 15 minutes after the start of dosing of n-butyllithium, the dosing of 847.9 g of a 1.17 molar solution of zinc chloride in THF (992 mmol) was started. The dosing rates of n-butyllithium and the ZnCl$_2$ solution were set so that an excess of already formed 2,2,6,6,-tetramethylpiperidine-Li was always present. The inlet locations for n-butyllithium and the solution of zinc chloride in THF were situated so that they were not directly next to one another. The reaction temperature fluctuated between 0 and 15° C. despite cooling. After dosing of the two reactants was completed, the reaction mixture was heated to room temperature and stirred for an additional 30 minutes. The slightly cloudy product solution was filtered through a filter until clear.
Starting weight: 1451.2 g
Active base: 0.54 mmol/g IMP-ZnCl*LiCl
Yield: 83.2% (relative to n-butyllithium used)

The invention claimed is:
1. A method for preparing a compound of formula

$$R^1R^2N\text{—}ZnY*LiY \qquad (I)$$

comprising the steps of
   dissolving a primary or secondary amine in an aprotic organic solvent,
wherein
a) the amine is provided in a concentration range of 10 to 90% by weight, and
b) a ZnY$_2$ solution in an aprotic organic solvent and a lithium base, R$^x$Li are simultaneously metered in,
wherein the dosing of the R$^x$Li is started first, and only after 5-10 mol-% R$^x$Li has been added is the metering of the ZnY$_2$ solution begun, and during the dosing phase, R$^x$Li and the ZnY$_2$ solution are dosed at different locations in the reaction solution; and
wherein
   R$^1$ and R$^2$ are independently selected from H, substituted or unsubstituted aryl or heteroaryl containing one or more heteroatoms, a linear, branched, or cyclic substituted or unsubstituted alkyl, alkenyl, alkynyl, or the silyl derivatives thereof; wherein R$^1$ and R$^2$ may together form a cyclic or polymeric structure in which at least one of the radicals R$^1$ and R$^2$ is not H;
   Y is selected from the group consisting F; Cl; Br; I; CN; SCN; NCO; HalO$_z$, where z is 3 or 4 and Hal is selected from Cl, Br, and I; NO$_3$; BF$_4$; PF$_6$; H; a carboxylate of the general formula R$^x$CO$_2$; an alcoholate of the general formula OR$^x$; a thiolate of the general formula SR$^x$; R$^x$P(O)O$_2$; or SCOR$^x$; or SCSR$^x$; O$_m$SR$^x$, where m is 2 or 3; or NO$_n$, where n is 2 or 3; and derivatives thereof; where Fe is a substituted or unsubstituted aryl or heteroaryl containing one or more heteroatoms, a linear, branched, or cyclic substituted or unsubstituted alkyl, alkenyl, alkynyl, or the derivatives thereof, or H.

2. A method according to claim 1, wherein the reaction is carried out continuously in a micro- or meso-flow reactor.

3. A method according to claim 1, wherein the R$^x$Li is used as a concentrate>95% by weight in an aprotic organic solvent.

4. A method according to claim 1, wherein Y are independent of one another, or both are Cl, Br, or I.

5. A method according to claim 1, wherein the lithium base is n-butyl-Li.

6. A method according to claim 1, wherein the solvent is selected from the group consisting of a cyclic ether, a linear ether, a branched monoether, a branched polyether, a thioether, an amine and a phosphine, or a derivative thereof which contain at least one heteroatom selected from O, N, S, and P.

7. A method according to claim 1, wherein the solvent comprises a member from the group consisting of tetrahydrofuran, 2-methyltetrahydrofuran, dibutyl ether, diethyl ether, tert-butylmethyl ether, dimethoxyethane, a dioxane, triethylamine, ethyldiisopropylamine, dimethyl sulfide, dibutyl sulfide, a cyclic amide, a cyclic alkane, a cyclic alkene, a linear alkane, a linear alkene, a branched alkane, a branched alkene, a urea derivative, an aromatic hydrocarbon, a heteroaromatic hydrocarbon and an aliphatic hydrocarbon.

8. A method according to claim 1, wherein the solvent comprises a member from the group consisting of 1,4-dioxane, dichloromethane, 1,2-dichloroethane, $CCl_4$; N,N'-dimethylpropylene urea, benzene, toluene, xylene, pyridine, pentane, cyclohexane, hexane, heptane; hexamethylphosphoric triamide and $CS_2$.

9. A method according to claim 1, wherein both Y are Cl.

10. A method according to claim 1, wherein the solvent is a cyclic amide selected from the group consisting of N-methyl-2-pyrrolidone, N-ethyl-2-pyrrolidone and N-butyl-2-pyrrolidone.

\* \* \* \* \*